US006663902B1

(12) United States Patent
Hei et al.

(10) Patent No.: US 6,663,902 B1
(45) Date of Patent: Dec. 16, 2003

(54) METHOD AND COMPOSITION FOR THE GENERATION OF CHLORINE DIOXIDE USING IODO-COMPOUNDS, AND METHODS OF USE

(75) Inventors: Robert D. P. Hei, Baldwin, WI (US); David Daniel McSherry, St. Paul, MN (US); Kim R. Smith, Woodbury, MN (US); Keith E. Olson, Apple Valley, MN (US)

(73) Assignee: Ecolab Inc., St. Paul, MN (US)

( * ) Notice: Subject to any disclaimer, the term of this patent is extended or adjusted under 35 U.S.C. 154(b) by 150 days.

(21) Appl. No.: 09/664,623

(22) Filed: Sep. 19, 2000

(51) Int. Cl.$^7$ .................... A01N 59/12; A01N 59/06; A01N 59/00; A61K 33/18; C11D 7/54; C01B 11/02; A61L 9/04; A23L 3/358

(52) U.S. Cl. ............... 424/661; 424/78.08; 424/78.17; 424/78.25; 424/667; 424/668; 424/669; 424/670; 424/671; 424/672; 424/613; 424/614; 424/615; 424/616; 424/660; 424/662; 424/663; 424/664; 424/665; 424/666; 424/677; 424/678; 424/679; 424/680; 424/681; 424/703; 424/713; 424/715; 424/723; 426/335; 426/532; 423/477; 510/111; 510/302; 510/303; 510/319; 510/379; 510/383; 510/385; 510/389; 422/29; 422/37; 514/553; 514/706; 514/714

(58) Field of Search .................. 424/661–665, 424/667–672, 78.08, 78.17, 78.25, 613–616, 660, 666, 677–681, 703, 713, 715, 723; 423/477; 422/37, 29; 426/335, 532; 510/111, 302, 303, 319, 379, 383, 385, 389; 514/553, 706, 714

(56) References Cited

U.S. PATENT DOCUMENTS

| | | | |
|---|---|---|---|
| 2,071,091 A | 2/1937 | Taylor ...................... 167/17 |
| 2,071,094 A | 2/1937 | Vincent .................... 167/17 |
| 2,482,891 A | 9/1949 | Aston ....................... 252/187 |
| 3,591,515 A | 7/1971 | Lovely ...................... 252/187 |
| 3,778,476 A | 12/1973 | Rembaum et al. ..... 260/576.6 P |
| 3,874,870 A | 4/1975 | Green et al. ................. 71/97 |
| 3,898,336 A | 8/1975 | Rembaum et al. ........... 424/25 |
| 3,931,319 A | 1/1976 | Green et al. ........ 260/567.6 P |
| 4,013,507 A | 3/1977 | Rembaum ................. 195/1.8 |
| 4,027,020 A | 5/1977 | Green et al. ........... 424/248.56 |
| 4,084,747 A | 4/1978 | Alliger ........................ 239/4 |
| 4,089,977 A | 5/1978 | Green et al. ............... 424/329 |
| 4,111,679 A | 9/1978 | Shair et al. .................. 71/67 |
| 4,330,531 A | 5/1982 | Alliger ...................... 424/149 |
| RE31,779 E | 12/1984 | Alliger ................... 252/187.23 |
| 4,506,081 A | 3/1985 | Fenyes et al. .............. 548/523 |
| 4,547,381 A | 10/1985 | Mason et al. .............. 426/316 |
| 4,575,491 A | 3/1986 | Pollack et al. ............. 436/125 |
| 4,581,058 A | 4/1986 | Fenyes et al. ................ 71/67 |
| 4,585,481 A | 4/1986 | Gupta et al. ............. 106/14.05 |
| 4,585,482 A | 4/1986 | Tice et al. ............... 106/15.05 |
| 4,689,167 A | 8/1987 | Collins et al. ................ 252/95 |
| 4,689,169 A | 8/1987 | Mason et al. ........... 252/186.24 |
| 4,778,813 A | 10/1988 | Fenyes et al. .............. 514/357 |
| 4,842,771 A | 6/1989 | Rorig et al. ................ 252/547 |
| 4,880,638 A | 11/1989 | Gorden ...................... 424/662 |
| 4,891,216 A | 1/1990 | Kross et al. .................. 424/78 |
| 4,956,184 A | 9/1990 | Kross |
| 4,970,211 A | 11/1990 | Fenyes et al. .............. 514/252 |
| 4,986,990 A | 1/1991 | Davidson et al. .......... 424/665 |
| 5,051,124 A | 9/1991 | Pera ............................ 71/67 |
| 5,055,219 A | 10/1991 | Smith ........................ 252/102 |
| 5,078,896 A | 1/1992 | Rorig et al. ................ 252/102 |
| 5,093,078 A | 3/1992 | Hollis et al. ................. 422/16 |
| 5,100,652 A | 3/1992 | Kross et al. ................. 424/53 |
| 5,165,910 A | 11/1992 | Oikawa et al. ............. 423/477 |
| 5,178,830 A | 1/1993 | Riera Aixala ................ 422/37 |
| 5,185,161 A | 2/1993 | Davidson et al. .......... 424/665 |
| 5,192,459 A | 3/1993 | Tell et al. ................... 252/106 |
| 5,227,306 A | 7/1993 | Eltomi et al. ................ 436/55 |
| 5,281,412 A | 1/1994 | Lukacovic et al. ........... 424/52 |
| 5,326,546 A | 7/1994 | Rosenblatt et al. ......... 423/241 |
| 5,336,426 A | 8/1994 | Rader et al. ................ 252/102 |
| 5,360,609 A | 11/1994 | Wellinghoff ............. 514/772.3 |
| 5,382,520 A | 1/1995 | Jenson et al. ................ 436/55 |
| 5,384,134 A | 1/1995 | Kross et al. ................ 424/661 |
| 5,389,390 A | 2/1995 | Kross ........................ 426/332 |
| 5,462,689 A | 10/1995 | Choy et al. .................. 252/90 |
| 5,534,266 A | 7/1996 | Ricketts ...................... 424/672 |
| 5,567,405 A | 10/1996 | Klatte et al. ................ 423/477 |
| 5,575,993 A | 11/1996 | Ward et al. ................ 424/78.1 |
| 5,597,793 A | 1/1997 | Besse et al. ................ 510/434 |
| 5,648,074 A | 7/1997 | Park et al. ................. 424/94.2 |
| 5,651,996 A | 7/1997 | Roozdar .................... 424/665 |
| 5,716,611 A | 2/1998 | Oshlack et al. .......... 424/78.25 |
| 5,720,984 A | 2/1998 | Ricketts ...................... 424/672 |
| 5,820,822 A | 10/1998 | Kross ........................... 422/37 |
| 5,853,689 A | 12/1998 | Klatte ........................ 423/478 |
| RE36,064 E | 1/1999 | Davidson et al. .......... 424/665 |
| 5,885,620 A | 3/1999 | Foret ......................... 424/669 |
| 5,916,581 A | 6/1999 | Foret et al. ................. 424/405 |
| 5,922,776 A | 7/1999 | Wellinghoff et al. ..... 514/772.3 |
| 5,965,264 A | 10/1999 | Barenberg et al. .......... 428/402 |
| 6,004,587 A | 12/1999 | Mullerat et al. ............ 424/661 |
| 6,231,830 B1 * | 5/2001 | Madray ...................... 423/477 |

FOREIGN PATENT DOCUMENTS

| WO | 98/38865 | 9/1998 |
|---|---|---|
| WO | 99/24356 | 5/1999 |

OTHER PUBLICATIONS

Kirk–Othmer Encyclopedia of Chemical Technology, John Wiley & Sons, New York, 4th ed., vol. 5, pp. 968–991 (1993).*

* cited by examiner

Primary Examiner—John Pak
(74) Attorney, Agent, or Firm—Vidas, Arrett & Steinkraus

(57) ABSTRACT

The present invention relates to a biocidal composition, designed for the generation of chlorine dioxide, comprising at least one iodo-compound having at least one iodine atom and a source of chlorite ions. The molar ration of chlorite ions to iodine atoms is 2 or greater. The composition finds use in a variety of applications including methods of cleaning, sanitizing, deodorizing, and disinfecting various surfaces.

43 Claims, No Drawings

METHOD AND COMPOSITION FOR THE GENERATION OF CHLORINE DIOXIDE USING IODO-COMPOUNDS, AND METHODS OF USE

FIELD OF THE INVENTION

This invention relates to a novel composition in which chlorine dioxide is generated, and to the use of such a composition in formulations specifically adapted for use in cleaning, sanitizing, deodorizing, and disinfecting surfaces into or onto which the material is to be applied. More particularly, the present invention relates to a novel composition and method for the generation of chlorine dioxide using iodo-compounds and chlorite ions, and to methods of using such a composition.

BACKGROUND OF THE INVENTION

Chlorine dioxide ($ClO_2$) is known to be extremely effective for use as an antimicrobial, disinfectant, deodorizer, sterilizer, sanitizer, fungicide, germicide, and so forth. One problem associated with chlorine dioxide, however, is that it exists in a gaseous state, and as such is difficult to transport commercially. Chlorine dioxide as a concentrated gas is explosive and poisonous.

One common method for using or incorporating chlorine dioxide gas has been to dissolve the gas in a liquid to form a solution and attempt to stabilize the dispersed gas using chemical adjuvants such as polyvinyl pyrollidone, metal complexes, inorganic salts, viscosifiers, and so forth. These methods have a number of drawbacks. The most common problem being that the chlorine dioxide gas tends to release from the solution so that its shelf-life is relatively short. Since some applications require hours, days, or even weeks of solution use time for the chlorine dioxide formulation, a strict regimen of gaseous reapplication would be necessary to ensure adequate chlorine dioxide concentrations over time, even with all the currently known solution stabilizing additives.

As a consequence, the common practice has evolved to generating chlorine dioxide right at the site where it is being used. Such generation methods are outlined in *Chlorine Dioxide, Chemistry and Environmental Impact of Oxychlorine Compounds*; Masschelein, W. J., Ann Arbor Science Inc., 1979, and typically employ the use of chlorine dioxide generating or liberating compounds such as chloric acid, chlorites and chlorates in applications in which chlorine dioxide is being used as a disinfectant, sterilizer, deodorizer, sanitizer, antiseptic, fungicide, germicide, and so forth.

The generation of chlorine dioxide from sodium chlorite or some other chlorine dioxide liberating compound can be broadly classified into three categories including the acidification of chlorites, the oxidation of chlorites, or the reduction of chlorites. Chlorine dioxide generation is thus usually activated by the addition of an acid, the addition of an oxidant like bleach (i.e. hypochlorite or hypochlorous acid), persulfate, or chlorine, or the addition of a reductant to chlorates (chemical or electrochemical).

Typically, however, the generation of chlorine dioxide has been accomplished either in the laboratory or at industrial levels at low pH values of 3 or less. Compositions that have a low pH are a problem for application to the skin of humans or animals such as teat dips because such acidity can cause skin irritation and burning. Additionally, acidic compositions can be corrosive to materials used in industrial equipment including metals, elastomers, plastics, cements and concretes, wovens, and so forth. Problems due to corrosion of equipment can obviously have a negative economical impact when chlorine dioxide is used as a sanitizer for industrial equipment. Raising the pH to levels at which there is no skin irritation results in compositions that generate chlorine dioxide at an undesirably slow rate, or favors secondary reaction routes which simultaneously produce other more undesirable chlorine species (e.g., chlorates, chlorides, chlorine gas, and so forth). For example, an equimolar mixture of potassium chlorate and hydrochloric acid yields chlorine dioxide to chlorine gas at a ratio of about 1.0:1.35.

Patents relating to acid catalysis include U.S. Re. Pat. No. 36,064, U.S. Pat. Nos. 4,585,481, 5,165,910, 5,651,996 and 5,853,689. As noted above, and reviewed in chapter 13 of Masschelein, W. J., the general rule is that the stronger the acid, the faster and more efficient the production of chlorine dioxide. For industrial applications, hydrochloric, sulfuric, or acetic are the most widely used acids, and the rate of chlorine dioxide generation and the overall yield of chlorine dioxide are improved using an excess of the acid (often up to 2–3 times excess). However, the lower the pH, the more corrosive the composition to equipment or treated surfaces, and the more irritation and burning to the skin of humans or animals. Comparatively, if the acid concentrations are reduced to concentrations that are too low, the rate of generation and the overall yield of chlorine dioxide are dramatically reduced to unusable levels.

A patent relating to the reduction of chlorates is U.S. Pat. No. 5,382,520. A patent relating to the oxidation of chlorites is U.S. Pat. No. 5,227,306 which describes a chlorite-chlorine system.

Other disadvantages to previously used methods of chlorine dioxide generation include the formation of undesirable secondary by-products such as chloride or chlorine, high equipment costs due to the complexity of the equipment required, and the potential of explosion from localized heat development or chlorine dioxide head-space gas development. Further disadvantages result from the handling, dispensing and regulation of poisonous chlorine gas.

Further, those antimicrobial agents which are lethal to microorganisms, can also be toxic in varying degrees to humans and animals in that both higher and lower forms of life share at least some common metabolic pathways.

Consequently, there remains a need for an effective means of generating chlorine dioxide in situ at pH values where skin irritation is not a problem, and the rate of chlorine dioxide generated is rapid, and the yield potentially long lasting.

Furthermore, there has been a long felt need for antimicrobial agents which have a high degree of antimicrobial efficacy, and which can be safely used, and pose no environmental incompatibility.

SUMMARY OF THE INVENTION

The present invention relates to a chlorine dioxide generating biocidal composition comprising a source at least one iodo-compound having at least one iodine atom, and a source of chlorite ions. The molar ratio of chlorite ions to iodine atoms is 2 or more. The composition rapidly generates chlorine dioxide over a broad pH range.

The present invention further relates to a two-part, chlorine dioxide generating composition prepared by mixing a first part and a second part. The first part comprises at least one iodo-compound having at least one iodine atom and the second part comprises a source of chlorite ions. Between the two separate parts at least one phase is a liquid, wax, or condensed-gas phase, or has at least one solvent. When the two parts are mixed, the reaction will proceed through a series of steps ultimately leading to chlorine dioxide generation.

Using the two-part generating system of the present invention can result in the generation of iodine, a first biocidal compound, which is subsequently followed, and ultimately replaced by the generation of chlorine dioxide, a second biocidal compound. The iodine is therefore lost during chlorine dioxide generation. The molar ratio of chlorite ions to iodine atoms is 2 or more after mixing the two parts.

The present invention further relates to a method for the production and delivery of chlorine dioxide in a condensed gas comprising the steps of providing a source of chlorite ions and providing at least one iodo-compound having at least one iodine atom wherein the molar ratio of chlorite ions to iodine atoms is 2 or greater. The composition may be produced in a gaseous form followed by compression, or may be produced in an already condensed gas.

The present invention further relates to a method of reducing the microbial population on a surface comprising contacting said surface with a non-aqueous gas or condensed gas comprising about 0.1 to about 100,000 ppm of a biocidal composition said composition comprising at least one iodo-compound having at least one iodine atom, and at least one source of chlorite ions. The molar ratio of chlorite ions to iodine atoms is 2 or greater.

Thus, the present invention may be used for the reduction of the viral or microbial population on just about any surface or object, for the reduction of such populations in liquids and gases, and for the reduction of such populations on both human and animal skin.

Surprisingly, the generation of chlorine dioxide using the method of the present invention occurs rapidly even at high pH values relative to currently available systems. The reaction can, however, be controlled using slow-release or step-pulsing method.

A distinct advantage of the present invention is that the reaction proceeds through a series of steps in which iodine in generated as an intermediate reactant, and chlorine dioxide is ultimately generated. Both iodine and chlorine dioxide are excellent antimicrobials. A dual active antimicrobial system offers a broader spectrum of biocidal activity.

The compositions of the present invention are valuable for sterilizing, sanitizing, disinfecting, and preserving.

The compositions of the present invention may be used in teat dips, hard surface cleaners, wash waters, bleaches, laundry liquids, plant treatment compositions, food treatment compositions, and so forth.

DETAILED DESCRIPTIONS OF THE PREFERRED EMBODIMENTS

The present invention resides in a composition for antimicrobial or antiviral use wherein the composition produces chlorine dioxide in situ using a reaction between an iodo-compound and a chlorite source.

The compositions of the present invention find use as sanitizers, disinfectants, preservatives, sterilizers, deodorizers, antiseptics, fungicides, germicides, viracide, tuberculoside and so forth. The term sterilize refers to a physical and/or chemical process capable of destroying all forms of life including bacteria, viruses, fungi and spores on inanimate surfaces.

The terms bactericidal and bacteriostatic refer to the degree of efficacy of an antimicrobial composition. This reference is an accepted laboratory protocol for the measurement of such efficacy. Antimicrobial compositions may effect two kinds of microbial cell damage. The first is a truly lethal, irreversible action resulting in complete microbial cell destruction or incapacitation. The second type of cell damage is reversible, such that if the organism is rendered free of the agent, it can again multiply. The former is termed bactericidal and the latter, bacteriostatic. Sanitizers, disinfectants, viracides, and tuberculocidal agents are, by definition, agents which provide bactericidal activity, as opposed to bacteriostatic activity.

The term disinfectant refers to an agent that kills all vegetative cells including most recognized pathogenic microorganisms. As such, it must pass a more stringent bactericidal test; the A.O.A.C. Use Dilution Methods, Official Methods of Analysis of the Association of Official Analytical Chemists, paragraph 955.14 and applicable sections, 15th Edition, 1990 (EPA Guideline 91-2). High level disinfectants include reductions in viruses, mycobacteria and other resistant pathogenic organisms.

A sanitizer is an agent that reduces the number of bacterial contaminants to safe levels as judged by public health requirements. Practically, a sanitizer must result in a 99.999% reduction (5 log order reduction) for given organisms as defined by *Germicidal and Detergent Sanitizing Action of Disinfectants, Official Methods of Analysis of the Association of Official Analytical Chemists*, paragraph 960.09 and applicable sections, 15th Edition, 1990 (EPA Guideline 91-2). In common practice, substances that are applied to food contact surfaces for antimicrobial purposes must meet this requirement.

The term "preservative" is used generally to describe any agent that extends, prolongs or enhances the shelf-life of storage life of both food and non-food products by retarding or preventing deterioration of flavor, odor, color, texture, appearance, nutritive value, or safety. A preservative therefore, as opposed to a sanitizer for instance, is generally described as inhibitory in nature, or is bacteriostatic.

Methods used for evaluating preservatives include the Minimum Inhibitory Method Concentration test and the Zone of Inhibition test. The principal differences between a preservative and a sanitizer are two-fold and include the mode of action used, and the exposure time. A preservative prevents growth rather than killing microorganisms and has an exposure time of days to months. In contrast, a sanitizer must provide 99.999% kill (5 log order) within 30 seconds at a nominal temperature of about 20° C. Ideally, a sanitizing agent or compound will possess several important properties in addition to its microbicidal efficacy. The sanitizer should be no-rinse after application, and have residual antimicrobial activity. Residual activity implies a film of sanitizing material which will continue to have antimicrobial effect if the treated surface is contaminated by microorganisms during a storage or lag period. The sanitizer should be odor free to prevent transfer of undesirable odors onto foodstuffs. The sanitizer should be composed of direct food additive materials which will not affect food if contamination occurs, nor affect humans should incidental ingestion result. In addition, the sanitizer should be composed of naturally occurring or innocuous ingredients, which are chemically compatible with the environment and cause no concern for toxic residues in downstream water.

Generally, the present invention relates to the generation of chlorine dioxide through the reaction of at least one iodo-compound having at least one iodine atom and at least one ionic chlorite compound. The iodo-compound may be referred to herein as an activator, promoter or initiator compound, and activates the chlorite compound to produce chlorine dioxide. Iodo-compounds will be used in the present specification to refer generally to any compound that has in its chemical structure, at least one iodine atom.

An example of a compound having at least one iodine atom is an iodide salt. Upon the addition of chlorite ions, it is generally believed that the reaction proceeds by the following oxidation-reduction reaction and may be illustrated by the following generalized (unbalanced) formula:

$$2(XClO_2^-)+XI^-\rightarrow[I_2]\rightarrow XIO_3^-+ClO_2$$

where $ClO_2^-$ is a negatively charged chlorite ion X (is a/are) cation(s), $I^-$ is an iodide anion, $I_2$ is molecular iodine, $IO_3^-$ is an iodate ion, and $ClO_2$ is chlorine dioxide (solvated or gaseous). While it is not the intent of this patent to conclusively identify the exact reaction mechanism, it is reasonable to suggest that the chlorite salt acts as an oxidant to convert, in situ, the iodide salt into labile iodine which, subsequently, is converted to iodate as the chlorine dioxide is formed. This mechanism is consistent with the generalization literature reaction between chlorite ions and halogens; as outlined in Furman, C. S. and Margerum, D. W.; Inorg. Chem., 1998, Vol. 37, pp. 4321–4327 and references therein. It is surmised that the following balanced equation may be representative of the ultimate reaction responsible for the generation of chlorine dioxide from sodium chlorite and an inorganic iodide salt:

$$4ClO^-_2+2H^++I^-\leftrightarrows 2Cl^-+2ClO_2+H_2O+IO^-_3$$

Other iodo-compound sources including elemental iodine, polyhalides, interhalides, and so forth, which are not broadly classified as an iodide salt, may or may not be represented by the same reaction scheme as illustrated above. The reaction scheme is intended as an illustration only, and not as an exclusive reaction mechanism for representing chlorine dioxide as generated according to the present invention. However, each type of iodo-compound yields chlorine dioxide in similar yields.

As already noted above, the iodo-compounds of the present invention act as activator, catalyst or promoter for the formation of chlorine dioxide from the chlorine-dioxide precursor compound.

Iodo-compounds useful herein include, but are not limited to, iodide salts, iodine, iodoform, hydrogen iodide, iodine containing interhalides, polyhalides including those with 2–9 iodine molecules, iodine-containing ionene resins or polymeric quaternary ammonium compounds, oxides of iodine, organo-iodides, iodophors, and so forth, and mixtures thereof.

The iodide salts useful herein are those having the following general formula:

$$MI_n$$

where M is a metal ion and is selected from alkali metals, alkaline earth metals, transition metals, and mixtures thereof, and n is a number equal to the metal valency.

Organo-iodides include, but are not limited to, short-chain aliphatic iodides, haloforms such as iodoform, iodoacetic acid, iodo silanes and siloxanes, iodoaromatics such as iodobenzene, 2-iodobenzoic acid, iodouracil, iodopyrazole, 6-iodo-2-picolin-5-ol, and so forth, and so forth.

Specific short-chain aliphatic iodides include $C_1$ to $C_8$ mono-poly iodides such as methyliodide, ethyliodide, diiodomethane, 2-iodoethanol, N-iodosuccinimide and so forth.

Other inorganic iodo-compounds include elemental iodine ($I_2$), the interhalides such as salts of IBr, ICl, $ICl_2$, and so forth, and the polyhalides such as salts of $B_uI_wBr_yCl_{y1}F_z$ wherein w is an integer from 0 to 8, y and y1 are each independently integers from 0 to 8, z is an integer from 0 to 1, $B_u$ is a non-halogen anion and u is an integer from 0 to 1.

The ionene polymers or polymeric quaternary ammonium compounds, also referred to as polyquats, are a large class of cationic polymers containing quaternary nitrogens in the polymer backbone. Biologically active ionene polymers for use in aqueous systems as microbicides, bactericides, algicides, sanitizers, and disinfectants are discussed in A. Rembaum, *Biological Activity of Ionene Polymers*, Applied Polymer Symposium No. 22, 299-317 (1973). Ionene polymers are also discussed in U.S. Pat. Nos. 3,778,476, 3,874,870, 3,898,336, 3,931,319, 4,013,507, 4,027,020, 4,089,977, 4,111,679, 4,506,081, 4,581,058, 4,778,813, 4,970,211, 5,051,124, 5,093,078, 5,575,993, and so forth. All of these patents as well as others relating to such polymers, are herein incorporated by reference in their entirety. Some examples of ionene polymers include: the epi-amines, the polymers of diallyldimethyl ammonium iodides, cationic polyacrylamides, etc., and copolymers of the aforementioned.

The term "iodophor" is used herein to refer generally to those compounds which are complexes of iodine, or may refer to any carrier of iodine, the only requirement being that the compounds have at least one iodine atom in their structure. Iodophors are typically formed with organic polymers or surfactants to improve the solubility of iodine in aqueous solution. These organic polymers include a broad range of molecular weights and chain lengths, and may be either ionic or non-ionic in character, and may possess either surfactant or non-surfactant properties. Polyvinylpyrrolidone and detergent polymers are known to increase the aqueous solubility of iodine and are perhaps the more commonly used polymers for iodophor formation. Polyvinylpyrrolidone is a non-detergent, non-ionic, non-surface active polymer. Detergent polymers, on the other hand, are nonionic, anionic and cationic, and are surface active. Iodophors are discussed in "Proceedings of the $2^{nd}$ International Symposium on Povidone" Univ. of Kentucky, Apr. 12–15, 1987; Lexington, Ky.; and patents U.S. Pat. Nos. 5,916,581, 5,885,620, 5,720,984, 5,716,611, 5,534,266, and 4,575,491 herein incorporated by reference. The iodo-compounds or activator component is useful in an amount effective to induce formation of chlorine dioxide in an amount effective for the composition to act as an antiseptic, disinfectant, deodorant, sanitizer, and so forth.

The chlorine dioxide precursor employed in the present invention is preferably a chlorite compound, and may be any metal chlorite, as well as mixtures thereof. The chlorite is preferably a salt of an alkali metal, an alkaline earth metal, a transition metal, or a mixture thereof. Examples of useful chlorites include sodium chlorite and potassium chlorite which are of the alkali metal class, and barium chlorite, calcium chlorite and magnesium chlorite which are of the alkaline earth metal class. Potassium chlorite and sodium chlorite, especially a dry technical grade sodium chlorite (typically contains about 80% by weight sodium chlorite and 20% by weight sodium chloride) are two of the preferred solid metal chlorites for use herein in powder, solid, or non-aqueous compositions. Liquid concentrate compositions using 2-part preparations preferably contain aqueous solutions of these metal chlorites in concentrations of about 0.01–75 wt %.

Preferably, the chlorine dioxide precursor components useful in the present invention are those which form or produce chlorine dioxide in a liquid medium in response to a an activator or promoter component. Typically, it is desirable to generate from about 0.1 ppm to about 5000 ppm of chlorine dioxide, preferably from about 1 to about 250 ppm, and most preferably from about 3 to about 150 ppm chlorine dioxide. Consequently, the amount of chlorite utilized is typically from about 0.5 to about 5000 ppm, and more preferably from about 10 to about 2500 ppm.

The chlorite compound, used in combination with an activator, i.e. iodo-compound, is preferably employed at a molar ratio of 2 or more to 1 of the chlorite compound to the iodo-compound if the iodo-compound has one iodine atom. The ratio is maintained by adjusting the chlorite concentration proportionately upward accordingly as the number of iodine atoms increases to two, three and so forth. Higher ratios (>2:1) (chlorite:iodo-compound) can also be used to make products which: 1) maintain a background chlorite residual or, 2) rapidly generate $ClO_2$, using initially the available iodo-compound, followed by slow generation using other generative or catalytic pathways (e.g., acid induced, metal ion catalyzed) inherent in the formulated product, or 3) allow for subsequent iodo-compound additions for "saw-tooth" chlorine dioxide generation profiles. Examples of this embodiment will be demonstrated in the examples.

The addition of chlorite to the iodo-compound, when the ratio of chlorite to iodine atoms is 2 or more, proceeds through a reaction in which, iodine, $I_2$, is first produced as noted by the yellowish-brown, brown, violet or mahogany color (solvent dependent color variations) produced in the solution. This color will vary depending on the concentration of the starting compounds, and the concentration of the iodine in the final solution. Of course, the more iodine, the darker the solution will be, with iodine odor being detectable during this phase of the reaction. Spectroscopic evidence of iodine and/or polyiodide species ($I_2$, $I_3^-$, $I_5^-$, etc.,) are verified in the ultraviolet-visible spectra. Subsequently, the solution then goes colorless-yellow followed by a yellowish-green color which is indicative of chlorine dioxide. Simultaneously, the distinct odor of chlorine dioxide is also noted with the yellowish-green color formation, and the ultraviolet-visible spectra contrast its ultimate formation versus the iodine intermediate. If the ratio of chlorite to iodine atoms is less than 2, only iodine is generated to any significant degree. The solution will remain a yellow-brown-violet color, and the ultraviolet-visible spectrum will indicate only the formation of iodine. For example, at a ratio of 2.5:1.0 chlorite to iodide, iodine quickly forms as evidenced by a darker yellow-brown color in aqueous solution. The color quickly fades to clear and then the solution is ultimately converted to a yellowish-green color which is indicative of the presence of chlorine dioxide.

In contrast to the present invention, many of the current methods of chlorine dioxide generation are through acid catalysis. If no iodo-compound is present, and the chlorite is added to an acidic solution, the solution remains clear. Chlorine dioxide may be generated over the course of time, but the reaction is much slower than that of the present invention. This novelty of the current art will be demonstrated in the examples.

Other optional ingredients may be added to the compositions of the present invention including defoamers, thickeners (also referred to as builders, viscosifiers or rheology modifiers), solidifiers, surfactants (also referred to as wetting agents or emulsifiers), emulsion stabilizers, defoamers, buffers, other antimicrobial agents, fungicides, emollients (skin conditioning or moisturizing agents), hydrotropes, humectants, preservatives, dyes, plasticizers, vitamin E, insect repellents, perfumes, waxes and so forth. An ingredient such as a dye may be added to the composition at the time of use as a separate tablet form, for instance. Such ingredients, and when and how much to use under varying conditions and in various compositions, are known to those of skill in the art, and do not need to be discussed in detail herein. However, some of these additives are discussed in more detail below.

One or more rheology modifiers may be added to the compositions of the present invention to enhance viscosity, or thicken and cause the aqueous treatment to cling to the surface being treated. An example of a thickened foam product is demonstrated in U.S. Pat. No. 5,597,793, which utilizes a polymer foam to lengthen clinging time on vertical surfaces. Clinging enables the composition to remain in contact with the transient and resident pathogenic bacteria for longer periods of time, thereby promoting microbiological efficacy and resisting waste because of excessive dripping. The rheology modifier may be a film former or may act cooperatively with a film forming agent to form a barrier that provides additional protection.

Preferred rheology modifiers include colloidal aluminum silicate, colloidal clays, polyvinyl pyrrolidone, polyvinyl acetate, polyvinyl alcohol, polyalkylene oxides, polyacrylamides, or mixtures thereof.

Water soluble or water dispersible rheology modifiers that are useful can be classified as inorganic or organic. The organic thickeners can further be divided into natural synthetic polymers with the latter still further subdivided into synthetic natural-based synthetic petroleum-based.

Organic thickeners are generally compounds such as colloidal magnesium aluminum silicate (Veegum), colloidal clays (Bentonites), or silicas (Cab-O-Sils) which have been fumed to create particles with large surface size ratios.

Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are slats of complex anionic polysaccharides. Synthetic natural-based thickeners having application are cellulosic derivatives wherein the free hydroxyl groups on the linear anhydro-glucose polymers have etherified or esterified to give a family of substances which dissolve in water and give viscous solutions. This group of materials includes the alkyl and hydroxyalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

All thickeners do not work with equal effectiveness in this invention. Preferred aqueous thickening agents are those which are extremely pseudoplastic (non-Newtonian, rapid relaxation), tend not to develop rigid three-dimensional structure from interpolymer interactions, have a low or negligible viscoelastic character and possess a high gel strength. Such Theological properties are manifested in a composition which has a smooth flowing appearance, is easy to pour and apply, coats uniformly without forming mucilage streamers as the applicator is withdrawn and remains firmly in place without significant sag. Examples of preferred rheology modifiers are xanthan gum and hydroxyalkylcelluloses.

Generally, the concentration of thickener used in the present invention will be dictated by the method of application. Spraying or misting requires a lower composition viscosity for easy and effective application of treatment than dipping. Film forming barrier dips typically require high apparent viscosity necessary to form thick coatings which insure improved prophylactic effect.

Additional film forming agents are included which typically work in conjunction with thickeners. In fact, many of the aforementioned rheology modifiers are themselves film formers of greater or lesser effectiveness; however, a preferred grade of polyvinyl alcohol when used with preferred thickeners such as xanthan gum or hydroxyalkylcelluloses affords particularly useful properties to compositions of this teaching, most notably the development of "balanced" films which are sufficiently water-sensitive to be stripped off with conventional washing, but capably adherent to withstand premature loss of integrity between applications. The success of the barriers thus formed by compositions of this invention are, in part, a consequence of a hydrophobic-hydrophilic balance, caused when non-volatile ingredients, especially fatty acids, surfactants and hydrotropes, become resident throughout the film and whose individual properties become additive with those characteristics of the thickeners and film formers. Such inclusions also plasticize the film and render it pliable.

Polyvinyl alcohol is a polyhydroxide polymer having a polymethylene backbone with pendent hydroxy groups. The monomer does not exist, so the polyvinyl alcohol moiety is made by first forming polyvinyl acetate and removing acetate groups using a base catalyzed methanolysis. Polyvinyl acetate polymerization is accomplished by conventional processes and the degree of hydrolysis is controlled by preventing completion of the methanol reaction. Such properties as film flexibility, water sensitivity, ease of salvation, viscosity, film strength and adhesion can be varied by adjusting the molecular weight and the degree of hydrolysis. The preferred polyvinyl alcohol for use in the compositions herein has a degree of hydrolysis greater than 92%, preferably greater than 98%, most preferably greater than 98.5%, and has a molecular weight that falls in the range of between about 15,000 and 100,000, and preferably between about 40,000 and 70,000 corresponding to a solution viscosity (4% wt aqueous solution measured in centipoise (cPs) at 20° C. by Hoeppler falling ball method) of 12–55 cPs (0.012 to 0.055 Pa·s) and 12–25 cP (0.012 to 0.025 Pa·s) respectively.

Solvents may be optionally used in the present invention depending on the form the compositions are supplied in and some useful solvents include, but are not limited to, water, glycerin, sorbitol, $C_1$ to $C_{22}$ carboxylic acids and carboxylic esters, $C_1$ to $C_{38}$ carboxylic diacids and carboxylic diesters, aromatic and aliphatic alcohols, glycols, ethers, glycol ethers and esters, and aliphatic branched or straight chain hydrocarbons, aromatic hydrocarbons and modified aromatic hydrocarbons such as phenolics, butylated hydroxytoluene (BHT), butylated hydroxyanisole (BHA) and PARABENS® including methyl, propyl, butyl and ethyl esters of p-hydroxybenzoic acid, condensible gases such as carbon dioxide, halocarbons, and so forth, and mixtures thereof. Certain fragrances may also be used for solvation.

Surfactants, liquid or solid, may also be optionally added to the compositions of the present invention including nonionic, cationic, anionic or amphoteric surfactants.

In specific embodiments in which the iodo-compound and the chlorite source are supplied in solid form, solidifying agents may also be added to the compositions of the present invention. These solidifying agents may either be organic or inorganic in nature. Additionally, some solidifying agents are capable of binding water, while others, such as waxes, are not.

Some examples of organic solidifying agents include polyethylene glycols, fatty acids, acetates, ureas, certain surfactants, defoamers and builders, and mixtures thereof.

Examples of inorganic solidifying agents come in the form of a hydratable inorganic salts. Some examples of salts useful herein include, but are not limited to, bicarbonates, carbonates, silicates, phosphates, sulfates and mixtures thereof.

Certain types of solidifying agents are capable of binding free water. This can be particularly useful during the processing of the compositions of the present invention, particularly in the case where a solid form is being produced. The presence of free water can cause the premature reaction of the iodo-compound and the chlorite ions. If the free water is bound, it becomes unavailable for the reaction.

Examples of solidifying agents capable of binding water include the organic polyethylene glycols, fatty acids, acetates and ureas, and the hydratable inorganic salts including the bicarbonates, carbonates, phosphates, silicates and sulfates. If hydratable salts are utilized, the amount of water used during processing is preferably less than that needed to convert all of the inorganic hydratable salt to a stable hydrate, and processing is accomplished at temperatures around 50° C.

Another alternative to prevent premature reaction during processing is to encapsulate one of the ingredients, i.e. either the iodo-compound or the chlorite source. Available forms in which the compositions may be supplied are discussed in more detail below, although such discussion is intended as illustrative and not exhaustive, and is not intended to limit the scope of the present invention in any way.

The types of additional ingredients required will be determined by the form that the composition is supplied in. One of skill in the art would understand which ingredients are necessary.

The chlorite may be added to the iodo-compound either in solid form wherein both the iodo-compound and the chlorite are solid, in liquid form, or as a gas, aerosol, or gel. A preferable solid form is a one-component powder system which may be later mixed in an aqueous solution. Another is a water soluble polymeric or inorganic based block or capsule or briquette or tablet which uses the solid-state to isolate and regulate the reaction rate. If supplied as a liquid, gas, aerosol, or gel, additional ingredients required include solvents, gelling agents, film forming agents, solidifying materials, and so forth.

Some specific embodiments of the present invention are discussed herein. For instance, in one embodiment of the present invention, chlorine dioxide is generated in a two-part system wherein a first part is mixed with a second part and wherein the first part comprises at least one iodo-compound having at least one iodine atom and the second part comprises a source of chlorite ions. Between the two separate parts at least one phase is a liquid, wax, or condensed-gas phase, or has at least one solvent. When the two parts are mixed the reaction will proceed through steps in which ultimately chlorine dioxide is produced. The invention also relates to two-part generating method where these steps include subsequent generation of iodine which is then replaced ultimately, and essentially completely, by chlorine dioxide. The molar ratio of chlorite ions to iodine atoms is 2 or more after mixing the two parts.

Another embodiment of the present invention is one in which there are sequential additions of iodo-compound to the chlorite part (multiple additions). The molar ratio of chlorite ions to iodine atoms for the total of all the iodo-compound additions is still 2 or more after mixing each addition.

In another embodiment of the present invention, a water-thickening two-part system is used. In this embodiment, an aqueous first part is mixed with an aqueous second part. The first part contains the iodo-compound having at least one iodine atom and the second part contains a source of chlorite ions. The first and/or second part will also contain a viscosity modifying agent that affects solution thickening upon the addition of water into the mixed phases.

Another embodiment of the present invention is a sustained or controlled release system of releasing chlorine dioxide. In this embodiment, one of the two parts may be stabilized, encapsulated, adsorbed, absorbed, coated, etc., and therefore maintained in a nonreactive state in some fashion. This can involve isolation of the reactants until use, or it can involve keeping the reactants in a nonaqueous media, or in a solid media, for instance. Upon contact of the reactants, or upon dissolution in water, the system will react and allows a slow or sustained release of chlorine dioxide. One of the parts contains at least one iodo-compound having at least one iodine atom and the other part contains a source of chlorite ions. At least one part uses a sustained release agent such as an encapsulating agent, zeolites, waxes, paraffins, inorganic or organic powders and aggregates, polymeric resins, permeable or soluble barrier films, and so forth. Upon mixing of the two parts, the reaction will proceed through steps in which ultimately chlorine dioxide is produced. However, the rate of chlorine dioxide generation is regulated by the sustained release agent. Again, as with the other embodiments discussed herein, the generation of iodine is ultimately, and essentially completely replaced, by chlorine dioxide. The molar ratio of chlorite ions to iodine atoms is 2 or more after mixing the two parts.

For sustained release, the compositions may be supplied in any physical form including solid, powder, liquid, gel, and so forth. However, stability issues usually require the compositions to be preferably supplied in either a solid/powder form, or as a gel or liquid that does not induce reaction. By this it is meant that the media should be non-aqueous until dilution into an aqueous stream. Using the liquid/gel systems requires that the iodo-compound and the chlorite source be isolated from one another. This can involve the independent isolation on-or-into an inorganic zeolite cage, inorganic clay, resin substrate or molecular sieve all of which are dispersed into a non reactive organic gel or liquid phase. The organic gel or liquid phase can be supplied in the form of mineral oils, organic esters, organic acids, non-aqueous surfactants, urea, polyoxyalkylene glycols, organic polymers, glycols or glycol-ethers, and so forth. The reactants may then be added to an aqueous stream for activation.

Methods of sustained release in a solid/powder-phase are discussed in U.S. Pat. No. 2,071,091 (solid compositions of metal chlorites and solid acids), U.S. Pat. No. 2,071,094 (dry briquettes of inorganic chlorites, a filler, and a solid acid), U.S. Pat. No. 2,482,891 (solid mixtures using chlorite salts, a desiccant material, and a solid organic acid anhydride), U.S. Pat. No. 3,591,515 (stabilized chlorite solutions on solid carriers that react with solid acids), U.S. Pat. No. 4,547,381 (dry sustained release compositions using an inert diluent, a chlorite salt, and a dry reaction agent), U.S. Pat. No. 4,585,482 (dry compositions and microcapsules using polymer shells around a chlorite salt and an organic acid), U.S. Pat. No. 5,567,405 (zeolite impregnated compositions that isolate the acid and chlorite components), U.S. Pat. No. 5,922,776 (water-free compositions containing acid releasing polymers, a hydrophilic material, and chlorite anions), U.S. Pat. No. 5,965,264 (powder sustained release compositions using molecular sieves and an acid releasing coating), and WO 98/38865 (compositions using dry solid inorganic hydrophilic materials like zeolites or clays to control chlorine dioxide formation upon exposure to water vapor) all of which are incorporated by reference herein in their entirety.

The above referenced methods can be used with the compositions of the present invention for generating chlorine dioxide. Using the compositions of the present invention, when in solid/powder form, the iodo-compounds are isolated from the chlorite ions until use of the composition wherein the generation of chlorine dioxide becomes desirable.

Other techniques that can be used to generate sustained levels of chlorine dioxide involve the use of permeable membranes which control the contact of reactants are described in WO 99/24356 and in U.S. Pat. No. 5,360,609 which are herein incorporated by reference in their entirety. Using this technology with the compositions of the present invention, the reactants, i.e. the iodo-compound and the chlorite ions, are in a solid/powder form and are contained in a sachet or water permeable membrane. The package is dropped into an aqueous solution at the time of use. As the aqueous solution permeates the membrane, the chlorite ions and the iodo-compound begin to react and generate chlorine dioxide which then emits from the membrane into the liquid water to produce the desired aqueous solution of chlorine dioxide. Optionally, solid acidulants may be added to the aqueous solution in either a solid or liquid form in order to increase the rate of reaction.

Surfactant film-forming technology may also be used for sustained release embodiments of the present invention. Surfactant-thickened systems are used which control the contact of reactants and consequently facilitate control of the evolution rate of chlorine dioxide. This type of technology is discussed in U.S. Pat. No. 4,842,771 and U.S. Pat. No. 5,078,896 (using a combination of cationic and anionic surfactant thickeners), U.S. Pat. No. 5,055,219 and U.S. Pat. No. 5,336,426 (quaternary compounds and organic counter ions), and U.S. Pat. No. 5,462,689 (amine oxides and organic counter ions) all of which are incorporated by reference herein in their entirety.

In a specific embodiment of the present invention, a two-component system is utilized and at least one of the chlorite and/or the iodo-compound, is carried in a liquid medium, at a predetermined concentration that is effective to produce the desired chlorine dioxide-containing composition. The liquid medium is preferably a solvent such as those described above. Desirable solvents include water, alkanes, lower alcohols such as ethanol, aromatic alcohols such as benzyl alcohol, glycols, glycol ethers and esters, terpenes, fragrances, PARABENS®, $C_1$ to $C_{18}$ fatty acids, esters and diesters, glycerin and $C_1$ to $C_{18}$ glycerin esters, $C_1$ to $C_{18}$ citrate esters, and so forth.

In liquid form, chlorite is typically stored in an alkaline solution to obtain improved shelf stability. Alkaline solutions can be, however, quite irritating to the skin. Acids or buffering agents may therefore be added to decrease the alkalinity, or even to neutralize the solution. If the chlorite compound is in a liquid form, the iodo-compound may also be offered in a liquid form, and the system will be a two-component system. The iodo-compound will typically be in an aqueous solution which may be acidified or buffered as well. Preferably, the solution is buffered to a near neutral pH of about 4–8.

Unlike many of the previously used chlorine dioxide generating systems, however, the compositions of the present invention, in contrast, are not dependent on pH for chlorine dioxide generation, and consequently, chlorine dioxide generation will occur at any pH from about 1 to about 11, and preferably about 2 to about 11. However, quite surprisingly the formation of chlorine dioxide using the compositions of the present invention occurs at an unexpectedly rapid rate even at near neutral pH values of about 4 to 8, and even in the range of 5–7. This is a surprising result in that typically, acid catalyzed production of chlorine dioxide takes place at an unacceptably low rate at such high pH values. However, the generation of chlorine dioxide using the compositions and methods of the present invention does occur more rapidly at certain pH values so that it is not entirely pH independent. Preferably chlorine dioxide generation using the compositions of the present invention is accomplished at a pH of about 3 to 9, and even more preferably, a pH of about 4 to 8 is employed.

Acid catalyzed production of chlorine dioxide, like many of the currently available systems, and in contrast to the present invention, typically only proceeds at a reasonable rate at much lower pH values of less than 3, and typically even around 0.5. Raising the pH will drastically increase the time required for chlorine dioxide generation to hours, days, or even weeks.

Optionally, acids or salts may be added to the present invention for controlling pH or for buffering, or as a background chlorine dioxide generation aide. Such acids or salts include, but are not limited to, aliphatic or olefinic carboxylic acids or carboxylate salts, aromatic carboxylic acids or salts, inorganic acids or salts, polymeric carboxylic acids or carboxylate salts, organic phosphonate or phosphate acids or salts, organic sulfonate or sulfate acids or salts, organic boric acids or salts, amino acids or salts, and so forth, and mixtures thereof.

Some more specific examples include acids or salts of boric, phosphoric, polyphosphoric, sulfuric, sulfamic, nitric, carbonic, and so forth, and mixtures thereof. Silicates are also useful. Other compounds useful herein include carboxylic acids, di/tri-carboxylic acids, hydroxy carboxylic acids, alpha-hydroxy carboxylic acids, and so forth, their salts, anhydrides, or esters thereof, and mixtures thereof. Others include glycolic, lactic, malic, citric, tartaric, acetic, diacetic, butyric, octanoic, heptanoic, nonanoic, decanoic, dodecanoic, malonic, adipic, succinic, salicylic, fumaric, maleic, acetoacetic, oxalacetic, pyruvic, α-ketoglutaric, and so forth, their salts, anhydrides or esters thereof, and mixtures thereof.

Mild acids are preferable for use herein. Some specifically preferred buffering compounds include lactic/lactate, citric/citrate, phosphoric/phosphate, boric/borate, sulfuric/bisulfate, succinic/succinate, or mixtures thereof of any of these acids with any of the salts. Such buffering agents are as noted above, however, quite optional.

In summary, the present invention offers a variety of forms in which it may be supplied including a one-component forms including solid, or a non-aqueous liquid, aerosol, gas, or gel system which may be added to an aqueous solution at a later date. The present invention may also be supplied as a two-component liquid system in which the chlorite compound is in one solution, and the iodo-compound is in a second solution. The solutions are then mixed at the time of use. Other two-component systems include aerosols, gases and gels.

Independent of the form used, the sequential generation of both iodine and chlorine dioxide in the present invention is an advantage in that two types of antimicrobials are generated in situ using ultimately one solution. Due to the dual antimicrobial nature of the system, there is a broader spectrum of microbials which the compositions of the present invention will be effective against. A combination of more than one antimicrobial is always better than using only one for broader spectrum coverage.

The compositions of the present invention may be utilized to reduce the microbial population on virtually any surface. The method involves contacting the surface with a liquid solution, aerosol, gel, wax, solid, powder, or gas comprising about 0.1 to about 100,000 ppm of the biocidal composition of the present invention.

The compositions of the present invention are effective against a wide variety of microorganisms. These include bacteria in either their vegetative or spore states and including gram negative, gram positive and acid fast bacteria. The compositions of the present invention are also antimicrobially active against bacteria, fungi, spores, yeasts, molds, mildews, protozoans, viruses, and so forth, including lipophilic, non-lipophilic, enveloped and naked RNA/DNA types.

Among others, the compositions of the present invention are effective against microbes including, but not limited to, viral members of Parvoviridae, Calciviridae, Herpesviridae, and Paramyxoviridae. Other bacterial organisms against which the compositions of the present invention are active include Enterobacteriaceae, Mycobacterium spp leading to tuberculosis (acid fast), Staphylococci including *Staphylococcus aureus* (gram positive), *Streptococcus pneumoniae, Streptococcus agalactiae, Klebsiella pneumoniae, Pseudomonas aeruginosa, Pneumocystic carinii, Listeria monocytogenes,* Aspergillus spp., *Echerischia coli* (gram negative) including O157:H7, Salmonella spp, *Bacillus cerius,* Chatomium spp, *Actinomyces pyogenes, Corynebacterium bovis,* human parainfluenza viruses, *Listeria monocytogenes,* nonenveloped double-shelled viruses such as rotaviruses or adenoviruses. *Pseudomonas aeruginosa, Mycoplasma bovis,* respiratory syncytial virus, *Haemophilus influenzae* Type B, other viruses including *parvovirus, coxsackie* virus or herpes virus, as well as other species of microorganisms and viruses. This list is illustrative of types of microbes which the present invention may be used to treat but is by no means an exclusive list. Both iodine and chlorine dioxide are broad spectrum antimicrobials. One of skill in the art would know what microbes against which such compounds are effective. The present invention envisions other microbes, not listed here, against which such compounds would be active, and does not intend to limit the scope of the invention in any way by such a list.

In general, the compositions according to the present invention are useful in reducing microbial or viral populations on surfaces or objects, in liquids and gases, on the skin of humans and animals, and so forth. They are also useful in reducing odors. They may be utilized in cleaning and sanitizing applications relating to the food industry, hospitality industry, medical industry, and so forth. More specifically, industrial and commercial applications in which the compositions find use include ware wash machines and dishware, cooling towers, pools, spas, fountains, industrial process waters, boilers, and so forth.

More specifically, the compositions of the present invention find use in any type of domestic and industrial cleaning compositions, including detergents, bleaches, hard surface cleaners, sanitizers, disinfectants, sterilants, hand soaps, textile sanitizers and bleaches, and so forth. The compositions also find use in solutions such that hospitals and related institutions may use such as antiseptics, sanitizing solutions, disinfectants, pre-surgical scrubs, and so forth.

The compositions of the present invention also find use in veterinary products for use on mammalian skin including teat dips, skin disinfectants and scrubs, mouth treatment products, foot or hoof treatment products (e.g., hairy hoof wart disease), ear and eye disease treatment products, post- or pre-surgical scrubs, disinfectants, sanitizing or disinfecting of animal enclosures, pens, veterinarian treatment areas (inspection tables, operation rooms, pens, and so forth,), and so forth.

The compositions can also be used to reduce microbes and odors in animal feeds, in animal watering stations and enclosures, in animal veterinarian clinics, animal surgical areas, and to reduce animal or human pathogenic (or opportunistic) microbes and viruses on animals. The compositions can also be used to reduce opportunistic pathogenic microbes on eggs.

The compositions of the present invention may also be used to treat animal carcasses. The compositions are preferably aqueous and have a concentration of 0.1 to about 100,000 ppm of the biocidal composition. In use, the aqueous materials are typically contacted with soiled or cleaned target surfaces.

The compositions of the present invention may be used for the treatment of various foods and plant species to reduce the microbial populations on such items, treatment of manufacturing or processing sites handling such species, or in the process waters around such foods and plants. Specifically, the present compositions may be used for treating areas where plants and animals are grown such as the soils or water (i.e. hydroponic) in which they are grown, treating food processing equipment, flume waters, retort waters, rinse waters, bottle chillers, warmers, third sink washing and santizing, cutting areas such as water knives, slicers, cutters and saws, cutting board additives, retort systems, egg washers, heaters, bottle washers, aseptic wash waters, belt sprays for food transport lines, boot and hand-wash dip-pans, food storage facilities, anti-spoilage air circulation systems, food refrigeration and cooler cleaners and santizers, beverage chillers and warmers, meat chilling or scalding waters, sanitizing gels, cooling towers, food processing antimicrobial garment sprays, blancher cleaning and sanitizing, non-to-low-aqueous food preparation lubricants, oils and rinse additives, aseptic packaging sanitizing applications, and so forth.

The compositions of the present invention may be used to treat any surfaces with which food might come into contact including packaging such as cartons, bottles, aseptic packages and films, dish ware such as glasses, plates, utensils, pots, pans, and so forth, sinks, transportation vehicles, processing equipment, and so forth.

These are only some of the many types of applications relating to the food industry in which the present compositions may be utilized for sanitizing and cleaning and is not intended as an exclusive list.

Particularly relevant food products include eggs, meats, seeds, leaves, fruits and vegetables. Plant surfaces include both harvested and growing leaves, roots, seeds, skins or shells, stems, stalks, tubers, corms, fruit, and so forth.

Many of the previously mentioned applications include hard surface cleaning. Hard surfaces include those surfaces comprised of glass, ceramic, metal, natural and synthetic rock, wood, and polymeric surfaces including those that are elastomeric or plastic in nature.

Such surfaces can be found on exposed environmental surfaces such as tables, floors, walls, and other mobile surfaces such as dish ware including pots, pans, knives, forks, spoons, plates, dishes, food preparation equipment such as tanks, vats, lines, pumps, hoses, and other processing equipment.

Other hard surface cleaning applications include clean-in-place systems (CIP), clean-out-of-place systems (COP), ware wash machines, washer/decontaminators, sterilizers, textile laundry machines, ultra and nano-filtration systems, indoor air filters, and so forth.

The soils most common to hard surface cleaning in the institutional and industrial environment include organic soils and inorganic soils or some mixture thereof. Such soils include food soils, water hardness soils, microbial biofouling, oil or grease contamination, and so forth.

The chlorine dioxide generating aqueous compositions can be contacted with soiled or cleaned surfaces using virtually any technique known to those in the art. For instance, the compositions may be sprayed onto a surface, surfaces may be dipped into the aqueous solution, cleaning compositions may be used in automatic ware washing machines or other batch-type processing. These applications are for illustrative purposes only and are not intended as a limitation on the scope of the present invention. For such applications, the concentration of chlorine dioxide may range from about 0.1 to about 500 ppm.

COP systems can include readily accessible systems including wash tanks, soaking vessels, mop buckets, holding tanks, scrub sinks, vehicle parts washers, non-continuous batch washers and the like.

CIP systems are important for use in modem food processing which utilizes a variety of continuous and semi-continuous processing units. The units are typically run in a substantially continuous manner of up to 24 hours a day to achieve maximum productivity and improve economic efficiency. The safe and effective operation of such process units requires periodic maintenance and cleaning. Regular maintenance and cleaning ensures that the equipment operates efficiently and does not introduce bacterial or other contamination into the food product food sources such as soil residue.

Commonly the processing units are made from hard surface engineering materials incluing metals such as steel, aluminum, or stainless steel, glass, synthetic substances such as acrylic based, plastics, epoxies, polyimide condensation products, and so forth, or some combination thereof. Contamination can occur on an exterior hard surface or on the interior surface of pipes, pumps, tanks, and other processing units.

The compositions of the present invention can be used in such process equipment using known cleaning methods for aqueous cleaning materials that can be applied in a variety of ways to an exterior hard surface or to an interior surface within such units.

The compositions of the present invention can be effectively used to clean and sanitize in clean-in-place (CIP) systems. CIP methods are commonly used to sanitize and/or clean continuous processing units. Using CIP methods, aqueous solutions are pumped through the CIP processing equipment in order to clean and sanitize the surfaces of food processing equipment without any substantial dismantling of the tanks, pumps, valves or pipe work of the processing equipment. CIP procedures tend to be easier to control and are more reproduceable than their manual counterparts. The choice of an effective aqueous cleaning composition is critical to the success of the cleaning procedure because the effectiveness of the procedure depends on the degree of chemical action of the ingredients found in the cleaning solution, and also on the mechanical impact of the spray on the residue.

During a CIP procedure, an initial aqueous rinse is passed through the processing equipment followed by a sanitizing/cleaning using the chlorine dioxide generating composition of the present invention in an aqueous solution. The flow rate of the material through the equipment is dependent on the equipment configuration and pump size. Flow rates in the range of 10 to 150 gallons per minute are common. The procedure is usually accomplished at ambient temperatures of about 70°–77° F. (about 20°–25° C.) The compositions of the present invention are effective in CIP systems and in order to achieve complete sanitizing and cleaning, the material should be contacted with the soiled surfaces for at least about 15 seconds, and preferably about 30–120 seconds.

The compositions of the present invention find particular utility in the cleaning/santizing of dairy processing equipment. Such equipment is commonly manufactured from glass or stainless steel, and is used in both dairy farm installations and in dairy plant installations for the processing of milk, cheese, ice cream or other dairy products. Use concentrations capable of generating from about 1 to 1000 ppm chlorine dioxide are preferred, with concentrations of about 5 to 300 being most preferred.

The compositions of the present invention are also effective antimicrobial and antiviral agents for sanitizing and disinfecting surfaces and air streams typically encountered in hospital settings including surgical, infirmity, birthing, mortuary, and clinical diagnosis rooms. These surfaces can be also characterized as "hard surfaces" and include walls, floors, hospital room equipment such as bed-pans, or woven and non-woven surfaces including surgical garments, draperies, bed linens, bandages, and so forth, or patient-care equipment such as respirators, diagnostic equipment, shunts, body scopes, wheel chairs, beds, and so forth, or the plethora of other surgical and diagnostic equipment.

The compositions can also be used to reduce odors and microbial or viral populations on surfaces or in gaseous streams, bleaching or reducing microbial or viral populations on woven or non-woven substrates, and treating skin diseases of, or on, animals and particularly on mammals, and so forth.

The compositions can also be used to effectively treat those microbes which spread via air or surface substrates, such as disease from fungi, molds, bacteria, spores and viruses. These communicable skin diseases can include athletes foot fungus and hairy hoof wart disease, mastitis or other mammalian milking diseases. Mastitis can be caused by a vast number of organisms of which the compositions of the present invention will exhibit antimicrobial activity.

The compositions can also be used to reduce microbial and viral counts in air and liquids by incorporation into filtering media or breathing filters. Especially useful is for removal of water and air-born pathogens such as Legionella.

Additionally, the compositions are effective by themselves, or mixed with other adjuvants, in reducing microbial and viral populations in applications in the food, hospitality and industrial markets. The compositions can also be used to reduce microbes and odors in recreational waters such as pools, spas, recreational flumes and water slides, fountains, and the like.

The following nonlimiting examples are further illustrative of the present invention and are not intended to limit in any way, the scope of the present invention.

EXAMPLES

Examples 1–11

Tables 1 and 2 illustrate the novelty of the present invention. The present invention generates chlorine dioxide via an unexpected and surprising route rather than through the typical iodide oxidation route to iodine, iodate, or other iodo-species.

The following experiments were prepared by adding various predetermined amounts of an alkaline solution of sodium chlorite to various predetermined amounts of a potassium iodide solution. These compositions are shown in Tables 1 and 2, columns 2–3.

All of the resultant solutions were buffered to a pH of 5 using a citric acid/sodium citrate solution with the exception of example 6 which was buffered using monopotassium dihydrogen phosphate. The reaction was allowed to proceed for 5 minutes and the iodine and chlorine dioxide generation were measured. Both iodine and chlorine dioxide formation began before 5 minutes. However, the measurements were recorded at this time because the color development appeared to be complete.

Solution active iodine was measured in hexane solution using extraction and subsequent optical absorption at wavelength of 520 nm. Solution active chlorine dioxide was measured using optical absorption at a wavelength of 360 nm.

Iodine forming solutions are titrated with a standard starch-thiosulfate method and chlorine dioxide containing solutions are titrated with a standard iodide-starch-thiosulfate method.

The data illustrates that at ratios of chlorite to iodide ion above about 2, appreciable amounts of chlorine dioxide are generated very rapidly, i.e. within less than about 5 minutes of mixing providing that the ratio of chlorite to iodide ion is greater than 2. Note in particular examples 1–6 and 7–11. At ratios of less than about 2:1, either no reactions occurred as illustrated by comparative examples A and B, iodide was converted to iodine as exhibited by the gold-violet colors, or to iodate as exhibited by the colorless solutions (comparative examples C to G). There was no evidence of chlorine dioxide, however, for any of these comparative examples.

Examples 1–11 exhibited chlorine dioxide generation as exhibited by the yellowish green color, as well as an in situ gold-brown color which occurred temporarily prior to final chlorine dioxide color formation, a color which is indicative of the presence of iodine prior to the endpoint formation of chlorine dioxide. This color behavior was not exhibited by any of the comparative examples. The chemical moieties were then verified at the different color points using the aforementioned spectroscopic method.

Also, while maintaining a constant level of iodide, it appears that the yields of chlorine dioxide—while being dependant on the ratio of chlorite to iodide of about 2 or greater—are more related to iodide level than to the iodide/chlorite ratio as exhibited by examples 3–5 and 7–11 which rise slowly, or even level off in yield, with increasing chlorite concentrations. Thus, it is illustrated in examples 7–11 that utilizing a 1500% increase in chlorite concentration while maintaining a constant iodide level, exhibits only a 70% increase in chlorine dioxide production. However, the data demonstrates that excess chlorite does not interfere with chlorine dioxide production. Additionally, the data demonstrates (examples 5 and 6) that these systems generate chorine dioxide independent of the buffering system.

Comparative example B prepared according to U.S. Re. Pat. No. 36,064 was used as a control to determine the background hydroxy-acid generation rate relative to the examples of the present invention. Comparative A produced no iodine or chlorine dioxide, while comparative B illustrated that a solution having only chlorite present produced no appreciable quantity of chlorine dioxide over a 5 minute period but rather only a hydroxy-acid catalyzed route as described in U.S. Re. Pat. No. 36,064.

TABLE 1

Effect Of Iodide And Varying Levels Of Chlorite, On Chlorine Dioxide Generation

| Example | NaClO$_2$ (ppm)[1] | KI (ppm) | Molar Ratio (ClO$_2$/I)[2] | Solution Color | Product Formation I$_2$ (ppm) | ClO$_2$ (ppm) |
|---|---|---|---|---|---|---|
| Comp A | 0 | 500 | 0 | Colorless | 0 | 0 |
| Comp B[3] | 1000 | 0 | 0 | Colorless | 0 | <1 (NM)[4] |
| Comp C | 100 | 500 | 0.30 | deep gold | 10 | 0 |
| Comp D | 200 | 500 | 0.59 | Colorless | 0 | 0 |
| Comp E | 400 | 500 | 1.199 | Colorless | 0 | 0 |
| Comp F | 500 | 500 | 1.48 | Colorless | 0 | 0 |
| Comp G | 600 | 500 | 1.78 | Violet | 20 | 0 |
| Ex 1 | 800 | 500 | 2.37 | green-violet | 0 | 19 |
| Ex 2 | 1000 | 500 | 2.97 | yellow-green | 0 | 156 |
| Ex 3 | 1400 | 500 | 4.15 | yellow-green | 0 | 267 |
| Ex 4 | 1600 | 500 | 4.75 | yellow-green | 0 | 237 |
| Ex 5 | 2000 | 500 | 5.93 | yellow-green | 0 | 279 |
| Ex 6 | 2000 | 500 | 5.93[5] | yellow-green | 0 | 227 |

[1] The ppm level of sodium chlorite powder (80% active).
[2] The solution pH's were buffered to a pH of 5 using citric acid/sodium citrate.
[3] Hydroxy-acid generation rate as per US RE36064
[4] NM = none measured via visible, spectroscopic, or titration method during 5 minutes.
[5] Buffered to pH 5 with monopotassium dihydrogen phosphate

TABLE 2

Effect Of Iodide, And High Levels Of Chlorite, On Chlorine Dioxide Generation

| Example # | NaClO$_2$[1] (ppm) | KI (ppm) | Molar Ratio (ClO$_2$/I) | Solution color | Product Formation I$_2$ (ppm) | ClO$_2$ (ppm) |
|---|---|---|---|---|---|---|
| A | 0 | 500 | 0 | colorless | 0 | 0 |
| B[3] | 1000 | 0 | 0 | colorless | 0 | <1 (NM)[4] |
| 7 | 1000 | 200 | 7.4 | yellow-green | 0 | 99 |
| 8 | 2000 | 200 | 14.8 | yellow-green | 0 | 118 |
| 9 | 4000 | 200 | 29.7 | yellow-green | 0 | 137 |
| 10 | 3000 | 200 | 59.3 | yellow-green | 0 | 153 |
| 11 | 16000 | 200 | 123.1 | yellow-green | 0 | 168 |

[1] ppm level of sodium chorite powder (80% active).
[2] Solution pH was buffered to pH 5 using citric acid/sodium citrate.
[3] Hydroxy-acid generation rate as per US RE36064
[4] NM = none measured via visible, spectroscopic, or titration method during 5 minutes.

Examples 12–19

The examples shown in Table 3 were prepared and analyzed as in Examples 1–11. However, in examples 12–19, the level of sodium chlorite was fixed and the level of iodide was varied.

As in the previous set of examples 1–11, it was demonstrated that chlorine dioxide forms at molar ratios of chlorite to iodide ion of greater than about 2; i.e., examples 12–19 demonstrate that chlorine dioxide forms at ratios of chlorite to iodide ion of greater than about 2. As in the previous examples, reactions begin almost immediately. However, measurements were taken after about 5 minutes because the color appeared to be stable by this time.

Again, below the ratio of chlorite to iodide ion of greater than 2, either no reactions occurred (comparative examples A–B), or the expected conversion of iodide to iodine (orange-to-violet colors) or iodate (colorless) occurred (comparative examples H–N). Again, no chlorine dioxide was generated for any of the samples below the chlorite to iodide ion ratio of about 2. The data further shows that the yields of chlorine dioxide are dependant on both the ratio of chlorite to iodide (greater than about 2), and also on the absolute iodide level.

Again, as previously seen in examples 1–11, examples 12–19 generated both chlorine dioxide and iodine in situ as evidenced by the temporary gold-to-brown color prior to the final chlorine dioxide color formation of yellowish-green. The chemical moieties were verified using the aforementioned spectroscopic method.

TABLE 3

The Effect Of varying Levels Of Iodide On Chlorine Dioxide Generation

| Example | NaClO$_2$[1] (ppm) | KI (ppm) | Molar Ratio (ClO$_2$/I) | Solution color | Product Formation[2] I$_2$ (ppm) | ClO$_2$ (ppm) |
|---|---|---|---|---|---|---|
| A | 0 | 500 | 0 | colorless | 0 | 0 |
| B[3] | 1000 | 0 | 0 | colorless | 0 | <1 (NM)[4] |
| H | 1000 | 500 | 0 | colorless | 0 | 0 |
| I | 1000 | 2000 | 0.7 | deep red | 172 | 0 |
| J | 1000 | 1600 | 0.9 | deep red | 166 | 0 |
| K | 1000 | 1400 | 1.1 | orange-red | 162 | 0 |
| L | 1000 | 1200 | 1.2 | violet | 159 | 0 |
| M | 1000 | 1000 | 1.5 | maroon | 152 | 0 |
| N | 1000 | 800 | 1.8 | orange-red | 162 | 0 |
| 12 | 1000 | 600 | 2.5 | yellow-green | 0 | 40 |
| 13 | 1000 | 500 | 2.9 | yellow-green | 0 | 156 |
| 14 | 1000 | 400 | 3.7 | yellow-green | 0 | 102 |
| 15 | 1000 | 200 | 7.4 | yellow-green | 0 | 99 |
| 16 | 1000 | 100 | 14.8 | yellow-green | 0 | 62 |

TABLE 3-continued

The Effect Of varying Levels Of Iodide On Chlorine Dioxide Generation

| Example | NaClO$_2$[1] (ppm) | KI (ppm) | Molar Ratio (ClO$_2$/I) | Solution color | Product Formation[2] | |
|---|---|---|---|---|---|---|
| | | | | | I$_2$ (ppm) | ClO$_2$ (ppm) |
| 17 | 2000 | 200 | 14.8 | yellow-green | 0 | 114 |
| 18 | 2000 | 150 | 19.8 | yellow-green | 0 | 108 |
| 19 | 2000 | 100 | 29.7 | yellow-green | 0 | 78 |

[1]ppm level of sodium chlorite powder (80% active).
[2]Solution pH was buffered to 5 using citric acid/sodium citrate.
[3]Hydroxy-acid generation rate as per US RE36064
[4]NM = none measured via visable, spectroscopic, or titration method during 5 minutes.

Examples 20–32 and Comparative Example P

Table 5 illustrates the relative rate of formation of chlorine dioxide within antimicrobial skin conditioning products using a control, comparative P, which is illustrative of the state of the art, and examples of the present invention (20–23). The data is illustrative of the utility of the present invention. A standard skin treatment formula shown in Table 4, below, was spiked with various levels of potassium iodide ranging from 0 to 400 ppm and each of the resultant compositions were then activated with sodium chlorite (965 ppm in all samples). The relative rates of chlorine dioxide generation in the aqueous samples were measured over time using a UV-visible spectrophotometer.

The data shows a substantial increase in the rate of chlorine dioxide formation using an iodo-compound versus the hydroxy-acid control (examples 20–23 and comparative example P) at a relatively skin-neutral pH. Thus it is shown, that there is a substantial increase in the rate of chlorine dioxide formation in the examples of the present invention (20–23) using iodide-induced generation versus inducement of chlorine dioxide using the acidification route (comparative P). For instance, it is shown that the initial rate of chlorine dioxide measured at 1.5 minutes is enhanced by about 6–21 times using the method of the present invention versus that of the conventional hydroxy-acid generation as per U.S. Re. Pat. No. 36,064. This is a substantial improvement based on performance criteria suggesting about 30 ppm or greater chlorine dioxide generation to provide an effective reduction in microbial population. As shown in comparative P, the hydroxy-acid route achieves this level only after about 15 minutes of mixing, while the present invention using the iodide inducing route (examples 20–23) illustrated an acceptable yield of chlorine dioxide in about 1.5 minutes which is a 10 fold improvement over the hydroxy-acid inducing route.

Lowering the pH can enhance the yield of chlorine dioxide in either of the two different types of compositions described above. However, the lower the pH, the more likely that skin irritation and burning will occur. Examples 20–23 therefore illustrate one advantage of using the chlorine dioxide generating method and compositions of the present invention to produce chlorine dioxide rapidly without adverse skin effects. Most applications desire immediate generation of chlorine dioxide, i.e. within about 5 minutes of mixing.

Examples 20–23 also demonstrate the ability of the iodide enhanced formulas to generate a much higher total amount of chlorine dioxide from constant chlorite levels thus greater utilization of the active chlorite compound is achieved.

TABLE 4

Chlorine Dioxide Based Skin Treatment Product

| Product Compounds | Amount (wt. %) |
|---|---|
| nonionic surfactant | 2.0% |
| ethoxylated lanolin | 5.0% |
| linear dodecyl benzene sulfonate | 2.0% |
| propylene glycol (and/or glycerine) | 42.0% |
| potassium hydroxide (45%) | to pH = 4.7 |
| lactic and/or citric acid (88%) | 12.0% |
| preservative | 0.4% |
| dye | 0.2% optional |
| Water | Remainder |

TABLE 5

Effect Of Iodide On The Chlorine Dioxide Generation Rate In A Skin Conditioner

| Ex | NaClO$_2$ (ppm) | KI (ppm) | Chlorine Dioxide Generation Rate[2] (ppm) | | | | | | |
|---|---|---|---|---|---|---|---|---|---|
| | | | 0 (min.) | 1.5 (min.) | 2.5 (min.) | 5 (min.) | 15 (min.) | 30 (min.) | 4020 (min.) |
| O[3] | 0 | 0 | 0 | 0 | 0 | 0 | 0 | 0 | 0 |
| P[4] | 965 | 0 | 0 | 10 | 12 | 24 | 36 | 36 | 70 |
| 20 | 965 | 50 | 0 | 68 | 71 | 76 | 87 | 80 | 79 |
| 21 | 965 | 100 | 0 | 118 | 117 | 117 | 124 | 123 | 85 |
| 22 | 965 | 200 | 0 | 200 | 200 | 204 | 208 | 205 | 116 |
| 23 | 965 | 400 | 0 | 211 | 208 | 207 | 213 | 211 | 81 |

[1]The ppm level of sodium chlorite powder which is only 80% active.
[2]The solution pH's were buffered to pH = 4.7 with the formula.
[3]A control experiment without sodium chlorite additive.
[4]Hydroxy-acid generation rate as per US RE36064

Examples 24–28

Examples 24–28 shown in Table 7 demonstrate the relative rate of reaction for the iodide-induced chlorine dioxide reaction in a commercial teat dip. Thus, the iodide (400 ppm) containing teat dip shown Table 6 was activated with sodium chlorite (1000 ppm). The relative rate of chlorine dioxide generation in the teat dip was measured over time using UV-visible spectroscopy.

The data demonstrates the rapid, iodide-induced rate of formation of chlorine dioxide at a skin friendly pH of 4.7. Again, immediate product use is desired, and within a few minutes of mixing the iodide enhanced formulas can be successfully employed.

TABLE 6

Chlorine Dioxide Based Teat Dip Product

| Product Compounds | Amount (wt. %) |
|---|---|
| Glycerine | 12.0% |
| nonionic surfactant | 0.1% |
| Ethoxylated lanolin | 0.2% |
| linear alkyl benzene sulfonate | 0.5% |
| Urea | 3.0% |
| potassium iodide | 0.04% |
| thickeners[1] | 0.3% |
| phosphoric acid | 1.5% |
| acetic acid | 5.0% |
| preservative | 0.2% |
| dye | 0.3% |
| water | Remainder |
| potassium hydroxide (45%) | to pH = 4.7 |

[1]Interchangeably, polyvinylpyrollidone, xanthan gum, or other thickener.

TABLE 7

The Rate Of Formation Of Chlorine Dioxide In A Teat Dip

| Example | Reaction Time (minutes) | $ClO_2$ Yield (ppm) |
|---|---|---|
| 24 | 0 | 0 |
| 25 | 2 | 85 |
| 26 | 10 | 103 |
| 27 | 20 | 106 |
| 28 | 60 | 89 |

Examples 5, 29–31

Table 8 demonstrates the effect of using various halide salts on the chlorine dioxide generation yield. The reactions were run as in Examples 1–11 with chlorine dioxide being measured after 5 minutes of reaction time. As shown, some substitution of iodide with bromide or chloride results in a negative impact, or may even result in a complete inhibition upon a complete substitution, i.e. 100% KBr or KCl in place of KI.

TABLE 8

The Effect Of Other Halide Salts On The Iodide Induced Chlorine Dioxide Generation Yield

| Example | $NaClO_2$[1] (ppm) | KI (ppm) | KBr (ppm) | KCl (ppm) | $ClO_2$ yield[2] | $ClO_2$ yield % |
|---|---|---|---|---|---|---|
| A[3] | 0 | 500 | 0 | 0 | 0 | 0% |
| B[4] | 1000 | 0 | 0 | 0 | 0 | 0% |
| 5 | 2000 | 500 | 0 | 0 | 281 | 19% |
| 29 | 2000 | 375 | 125 | 0 | 165 | 11% |
| 30 | 2000 | 250 | 250 | 0 | 100 | 7% |
| 31 | 2000 | 125 | 375 | 0 | 50 | 3% |
| Q | 2000 | 0 | 500 | 0 | 0 | 0% |
| R | 2000 | 0 | 0 | 500 | 0 | 0% |

[1]The ppm level of sodium chlorite powder which is only 80% active.
[2]The solution pH's were buffered to pH = 5 with citric acid/sodium citrate.
[3]A control experiment without sodium chlorite additive.
[4]Hydroxy-acid generation rate as per US RE36064

Examples 5, 32–36

In examples 5, 32–36 shown in the following Table 9, the ratio of sodium chlorite to potassium iodide was held constant at a molar ratio of 5.9 while the total amount of both reactants was increased. The reactions were run as in example 1–11 with a chlorine dioxide determination at 5 minutes after beginning the reaction. As can be seen, an increasingly higher amount of chlorine dioxide was generated corresponding to the increased reactant concentrations. These examples also show that the yield % of chlorine dioxide is relatively constant over the entire reaction range with some drop-off in yield at very high reactant levels.

TABLE 9

The Effect Of Variable Reactant Concentrations On Chlorine Dioxide Generation Yields and Percent Yields

| Examples | $NaClO_2$[1] (ppm) | KI (ppm) | $ClO_2$ yield[2] (ppm) | $ClO_2$ % yield |
|---|---|---|---|---|
| 5 | 2000 | 500 | 287 | 19% |
| 32 | 4000 | 1000 | 647 | 22% |
| 33 | 8000 | 2000 | 1399 | 23% |
| 34 | 16000 | 4000 | 2786 | 23% |
| 35 | 32000 | 8000 | 5119 | 21% |
| 36 | 64000 | 16000 | 6932 | 14% |

[1]The ppm level of sodium chlorite powder which is only 80% active.
[2]The solution pH's were buffered to pH = 4.7 with citric acid/sodium citrate.

Examples 6, 37–39

Examples 5, 37–39 shown in Table 10 illustrate the generation of chlorine dioxide independent of the type of buffer system used. The reactions were run as previously with a chlorine dioxide determination after 5 minutes. As shown, the general chlorine dioxide yield is relatively independent of the buffer type or concentration, and actually appears to reduce if excess hydroxy-acid (citric) is present. The inorganic mono-potassium dihydrogen phosphate (mono-PDHP) yielded approximately the same amount of chlorine dioxide as the organic citrate buffer system.

TABLE 10

The Effect of the Buffer System on the Chlorine Dioxide Yield

| Example | $NaClO_2$[1] (ppm) | KI (ppm) | Citric Acid[2] (ppm) | $ClO_2$ yield (ppm) |
|---|---|---|---|---|
| 6 | 2000 | 500 | mono-PDHP | 227 |
| 37 | 2000 | 500 | 2.0 | 279 |
| 38 | 2000 | 500 | 4.0 | 271 |
| 39 | 2000 | 500 | 8.0 | 179 |

[1]The ppm level of sodium chlorite powder which is only 80% active.
[2]The solution pH's were buffered to pH = 5 with the buffer additive and NaOH.

Examples 40a–40d

Examples 40a–40d, found in Table 11, below, illustrate the use of another iodo-compound, iodine ($I_2$) as the activator with sodium chlorite. Iodine is readily available and typically more economical than an iodide salt. Comparing the yield data in Tables 9 and 10 illustrates that the generation of chlorine dioxide is approximately the same using either elemental iodine or an iodide salt (measured as in example 1). The same composition was made and tested four different times to demonstrate the reproducibility of the data.

TABLE 11

The Effect of Molecular Iodine on Chlorine Dioxide Yield

| Example | $NaClO_2^1$ (ppm) | $I_2^2$ (ppm) | $ClO_2$ yield$^3$ (ppm) | $ClO_2$ % yield |
|---|---|---|---|---|
| 40a | 1667 | 500 | 221 | 18 |
| 40b | 1667 | 500 | 221 | 18 |
| 40c | 1667 | 500 | 249 | 20 |
| 40d | 1667 | 500 | 265 | 21 |

$^1$ppm level of sodium chlorite powder (80% active).
$^2$The iodine is supplied in ethanol.
$^3$Solution pH was buffered to pH of 5 with the buffer additive and NaOH.

Examples 41–42

Chlorine dioxide can also be generated using sodium chlorite and stationary-phase immobilized iodine (a polyiodide). The solutions of sodium chlorite, Examples 41–42 (citric acid buffered to a pH=5), were eluted through a commercial water treatment cartridge containing the "immobilized" iodine. The results, found in Table 12, below, demonstrate the ability to continuously form an effluent stream containing chlorine dioxide.

Also, when comparing examples 41 and 42 it appears that the presence of ethanol promotes the formation of chlorine dioxide. A higher level of solution chlorine dioxide is found when ethanol is present despite the fact that the ethanol-free sample contains double the amount of chlorite. Ethanol is suspected of acting as a solvent for the bound iodine, thereby greatly enhancing the chlorite-iodine reaction yield.

TABLE 12

Chlorine Dioxide Generation From a Stationary Polyiodide Source

| Examples | $NaClO_2^1$ (ppm) | ethanol (wt %) | $ClO_2$ yield$^1$ (ppm) |
|---|---|---|---|
| 41 | 1000 | 0 | 3 |
| 42 | 500 | 50 | 11 |

$^1$based on the chlorine dioxide absorbance at 360 nm.

Examples 43–47 and Comparative Example S

Examples 43–47 found in Table 13, below, also illustrate the use of elemental iodine in a non-aqueous organic solvent mix (50/50 wt % mixture of hexane/ethanol and buffered to a pH of 5 with citric acid) for the rapid generation of chlorine dioxide. As illustrated by the data, along with an increasing concentration of sodium chlorite there is, generally, an increasing concentration of chlorine dioxide. Again, there appears to be a limit to the yield, primarily based on the iodine concentration. The chlorine dioxide yield % appears to reach a maximum (example 45) and then declines with a 4× increase in chlorite concentration, thus indicating the relative importance of the iodine level.

TABLE 13

Chlorine Dioxide Generation from Iodine

| Examples | $NaClO_2^1$ (ppm) | Iodine (ppm) | Molar Ratio ($ClO_2$/I) | $ClO_2$ yield$^2$ (ppm) | $ClO_2$ yield %$^2$ |
|---|---|---|---|---|---|
| S | 0 | 500 | 0 | 0 | 0% |
| 43 | 417 | 500 | 1.5 | 0 | 0% |
| 44 | 833 | 500 | 3.1 | 50 | 4% |
| 45 | 1667 | 500 | 6.1 | 323 | 25% |
| 46 | 3333 | 500 | 12.2 | 430 | 17% |
| 47 | 6667 | 500 | 24.4 | 409 | 8% |

$^1$Actual weight basis corrected for the 80% activity.
$^2$Based on the chlorine dioxide absorbance at 360 nm.
$^3$Based on chlorite ion weight.

Examples 48–50 and Comparative Example T

Examples 48–50, found in Table 14, below, demonstrate the ability to use a variety of iodo-compounds to activate chlorine dioxide generation. The results show that both polymeric iodine and covalently-bound iodine sources can be utilized to generate chlorine dioxide using the method and compositions of the present invention.

TABLE 14

Chlorine Dioxide Generation From Various Iodo-Compounds

| Examples | $NaClO_2^1$ (ppm) | iodo-compound | iodo-compound$^2$ (ppm) | $ClO_2$ yield$^2$ (ppm) |
|---|---|---|---|---|
| T | 5000 | None | 0 | 3 |
| 48 | 5000 | Iodoacetic acid | 10,000 | 363 |
| 49 | 5000 | iodized-PVP | 10,000 | 140 |
| 50 | 5000 | choline-ClI$_2$ | 10,000 | 420 |

$^1$Active level of sodium chlorite.
$^2$Aqueous solutions buffered to a pH of 5 with acetic acid/acetate.
$^3$Based on the chlorine dioxide absorbance at 360 nm.

Examples 51–52 and Comparative Example U

A base teat dip composition, found in Table 15, was used to prepare examples, 51 and 52. These examples illustrate the ability of the compositions of the present invention as effective antimicrobial products, and also illustrate the compatibility of the biocidal agents of the present invention with other biocidal agents.

The base teat dip composition, Table 15, was activated using different concentrations of sodium chlorite solution to initiate the reaction. The solutions were observed for chlorine dioxide formation. Table 16 illustrates these compositions and the data shown confirms the chlorite-to-iodide ratio requirement of greater than about 2:1 for effective chlorine dioxide generation in an antimicrobial product. The solutions were also tested for microbial efficacy against *E. coli* (ATCC 11229) using an organic soil challenge of 10% sterile milk (2% milk fat). The results showed log reductions of >6.9 for 15 seconds contact time and >6.9 for 30 seconds contact time.

The base formula is shown in Table 15 below.

TABLE 15

Dual Active Chlorine Dioxide Teat Dip Product

| Product Compounds | Amount (wt. %) |
|---|---|
| Glycerine | 14.0% |
| Nonionic surfactant | 0.1% |
| Ethoxylated lanolin | 0.1% |
| Sodium, octane sulfonate | 15.0% |

TABLE 15-continued

Dual Active Chlorine Dioxide Teat Dip Product

| Product Compounds | Amount (wt. %) |
|---|---|
| Urea | 0.5% |
| Potassium iodide | 0.04% |
| Thickeners[1] | 0.3% |
| Phosphoric acid | 1.5% |
| Citric/lactic/benzoic acids | 5.4% |
| Heptanoic acid | 1.5% |
| Dye | 0.3% |
| Sodium bisulfate | 0.003% |
| Water | remainder |
| Potassium hydroxide (45%) | to pH = 4.7 |

[1]The thickeners are interchangeable. For instance, polyvinylpyrrolidone, xanthan gum, or other thickeners may be used.

TABLE 16

Chlorine Dioxide Generation In a Dual Active Teat Dip

| Exp. # | NaClO$_2$[1] (ppm) | KI (ppm) | Molar Ratio (ClO$_2$/I) | Reaction Observations |
|---|---|---|---|---|
| U | 0 | 400 | 0 | no color change, no ClO$_2$ formation |
| 51 | 75 | 400 | 0.3 | yellow-brown I$_2$ color and smell, no ClO$_2$ |
| 52 | 5000 | 400 | 3.4 | yellow-green ClO$_2$ color and smell |

[1]Active level of sodium chlorite.

Example 53

A barrier teat dip composition was prepared and tested for microbial efficacy. The composition is found in the following Table 17. Barrier compositions are typically characterized as being aseptic, high viscosity, surface protecting products. The formula, containing 400 ppm potassium iodide, was actived with 1000 ppm sodium chlorite. The chlorine dioxide yield results of the testing are found in Table 18. The relative rate of kill of *E. Coli*, based on the ATC method 11229, was found to yield complete (5 log) kill at each of the reaction times after mixing.

TABLE 17

| Raw Material | Weight Percent |
|---|---|
| Elvanol ® 50-42 premix | 5.00 |
| Sodium benzoate | 0.15 |
| Kelzan ® T xanthan gum | 0.40 |
| technical grade propylene glycol | 5.00 |
| Abil ® B 8852 polyether siloxane | 0.50 |
| Urea (prilled) | 2.00 |
| Glycerine (95% USP) | 5.00 |
| citric acid, anhydrous | 1.00 |
| linear alcohol 9 mole ethoxylate | 0.10 |
| ethoxylated lanoline, 75 ethylene oxide | 0.10 |
| lactic acid (food grade, 88%) | 0.25 |
| sodium alkyl sulfonate powder | 4.20 |
| isobornyl acetate | 0.10 |
| heptanoic acid | 1.00 |
| postassium hydroxide (liquid, 45%) | 1.02 |
| potassium iodide, USP | 0.04 |
| FD & C blue dye 1 | 0.06 |
| Remainder | deionized water |

TABLE 18

| Reaction Time (minutes) | ClO$_2$ Yield (ppm) | *E. Coli* Log Reduction |
|---|---|---|
| 0 | 0 | — |
| 2 | 85 | >5 |
| 10 | 103 | >5 |
| 20 | 106 | >5 |
| 60 | 89 | >5 |

Example 54 and Comparative Examples V–X

Potassium iodide, in an amount of 800 ppm, was added to the base teat dip composition found in Table 15, above. The sample was then activated with 2000 ppm of sodium chlorite at a pH of 4.7. The sample was sent to a commercial skin testing laboratory to evaluate for skin irritation. The testing was accomplished using methods known to those of skill in the art. The sample exhibited a skin irritation reading of 0.5 after 15 minutes of contact. As is known in the art, a rating of <1.0 is deemed acceptable.

Comparative Examples Y–Z and AA–DD

Various halide oxidant salts were evaluated to determine the effect on the chlorine dioxide generation. The procedure as described in Example 1 was followed using a solution pH of 4.7 and 0.8. The chlorine dioxide generation was determined using wetted iodide test paper and olfactory analysis. Chlorine dioxide has a very distinct odor. As illustrated in the following Table 19, there is no evidence of chlorine dioxide generation using chlorate or perchlorate salts at any ratio relative to the iodide concentration.

TABLE 19

| Comparative Example | NaClO$_3$ (ppm) | NaClO$_4$ (ppm) | KI (ppm) | ClO$_2$ Yield pH = 4.7 | ClO$_2$ Yield pH = 0.8 |
|---|---|---|---|---|---|
| Y | 20,000 | 0 | 80,000 | 0 | 0 |
| Z | 0 | 20,000 | 80,000 | 0 | 0 |
| AA | 50,000 | 0 | 50,000 | 0 | 0 |
| BB | 0 | 50,000 | 50,000 | 0 | 0 |
| CC | 80,000 | 0 | 50,000 | 0 | 0 |
| DD | 0 | 30,000 | 20,000 | 0 | 0 |

Example 55

A slow release composition in a solid block form was prepared by melting 50 g of polyethylene glycol (PEG) having a molecular weight of 8000 g/mole at about 160° F. (about 71° C.). Potassium iodide (1.0 g), sodium chlorite (2.5 g) and disodium hydrogen phosphate (5.0 g) were each added with mixing to the heated PEG. The mixture was poured into a mold and allowed to cool to ambient temperature which resulted in a hard, white colored block. The block was placed into a beaker of water and no color change was noted. There was a slight chlorine dioxide odor after about 15 minutes. The final composition was 1.7% potassium iodide, 4.3% sodium chlorite, 8.5% disodium hydrogen phosphate and 85.5% PEG-8000.

Example 56

Example 56 was prepared using the same procedure as in example 55 except that potassium dihydrogen phosphate was used instead of disodium hydrogen phosphate. The block was again placed in a beaker of water. This time, the liquid exhibited a brown color, followed by a colorless liquid, and then ultimately turned a yellow/green color.

While the solution was a brown color, the distinct odor of iodine could be detected, and while the yellow/green color was exhibited, the solution had the distinct odor of chlorine dioxide. The solution was allowed to stand without any agitation. The solution shifted back and forth between the various colors over a period of about 1 hour. The final composition was 1.7% potassium iodide, 4.3% sodium chlorite, 8.5% potassium dihydrogen phosphate, and 85.5% PEG-8000.

Example 57

A rapid releasing solid was prepared by melting 100 g PEG-8000 at about 160° F. (about 71° C.). Potassium iodide (0.5 g), sodium chlorite (5 g), potassium dihydrogen phosphate (10 g) was added to the PEG-8000. The mixture was poured into a mold and allowed to cool to ambient temperature. This resulted in a hard white block. The block was placed into a beaker of water. The liquid rapidly formed a yellow/green solution indicating chlorine dioxide evolution. No color changes were indicated. The final composition was 0.5% potassium iodide, 4.3% sodium chlorite, 8.7% potassium dihydogen phosphate and 86.6% PEG-8000.

Example 58

A non-foaming hard surface cleaner emulsion was prepared using the composition found in Table 21, below. Examples of hard surface cleaners include those used in ware-wash, COP, surgical equipment, walls, floors, CIP, and so forth. Upon the addition of chlorite salt, a rapid (<10 seconds) generation of chlorine dioxide was observed, with chlorine dioxide concentration lasting for up to 1 week. The concentration of chlorine dioxide generated can be varied by varying the iodide concentration.

TABLE 21

| Raw Material | Weight Percent |
| --- | --- |
| Elvanol ® 50-42 premix | 5.00 |
| sodium benzoate | 0.15 |
| Kelzan ® T xanthan gum | 0.40 |
| propylene glycol, technical grade | 5.00 |
| Abil ® B 8852 polyether siloxane | 0.50 |
| urea, prilled | 2.00 |
| glycerine, 96% USP | 5.00 |
| anhydrous citric acid, fine granular, USP | 1.00 |
| linear alcohol 9 mole ethoxylate | 0.10 |
| ethoxylated lanolin, 75 ethylene oxide | 0.10 |
| lactic acid (food grade, 88%) | 0.25 |
| isoamyl acetate | 0.20 |
| heptanoic acid | 1.00 |
| potassium hydroxide (liquid, 45%) | 1.02 |
| potassium iodide, USP | 0.07 |
| FD & C blue dye 1 | 0.06 |
| deionized water | remainder |

What is claimed is:

1. A biocidal or bleaching composition capable of generating chlorine dioxide comprising:
   a) at least one iodo-compound having at least one iodine atom said iodo-compound selected from the group consisting of an iodine containing interhalide, an iodine containing ionene resin, an organo-iodide, an organic iodophor, and mixtures thereof; and
   b) a source of chlorite ions;
      wherein the molar ratio of chlorite ions to iodine atoms is 2 or greater.

2. The composition of claim 1 wherein said molar ratio of chlorite ions to iodine atoms is greater than 2.

3. The composition of claim 1 wherein said composition has a pH of about 2–11.

4. The composition of claim 1 wherein said composition has a pH of about 4–8.

5. The composition of claim 1 wherein said composition is in a form selected from the group consisting of aqueous liquid, non-aqueous liquid, gel, gas, aerosol and solid.

6. The composition of claim 1 wherein said composition is in a sustained release form.

7. The composition of claim 5 wherein said aqueous liquid is a bleach.

8. The composition of claim 5 wherein said solid is a powder.

9. A method of reducing microbial populations on a surface or object, the method comprising applying the antimicrobial formation of claim 1 to said surface or object.

10. The method of claim 9 wherein said surface is a hard surface.

11. The composition of claim 1 further comprising a bromide or chloride salt.

12. The composition of claim 1 further comprising at least one member selected from the group consisting of chlorates, hypochlorites, perchlorates, iodates, perborates, percarbonates, persulfates and mixtures thereof.

13. A two-part, biocidal or bleaching chlorine dioxide generating composition prepared by mixing a first part and a second part said composition comprising
   in the first part
      i) at least one iodo-compound having at least one iodine atom said iodo-compound selected from the group consisting of an iodine containing interhalide, an iodine containing ionene resin, an organo-iodide, an organic iodophor, and mixtures thereof;
      ii) at least one solvent; and
   in the second part
      i) a source of chlorite ions; and
      ii) at least one non-acidic solvent;
         wherein the molar ratio of chlorite ions to iodine atoms is 2 or greater after mixing said first part and said second part.

14. The composition of claim 13 wherein iodine is first generated and then chlorine dioxide is generated.

15. The composition of claim 13 wherein said solvent in the first part is selected from the group consisting of water, glycerin, sorbitol, $C_{1-12}$ carboxylic acids, $C_{1-22}$ carboxylic esters, $C_{1-10}$ carboxylic diacids, $C_{1-10}$ carboxylic diesters, alcohols, glycols, ethers, liquid nonionic surfactants, aliphatic hydrocarbons, aromatic hydrocarbons, carbon dioxide, fluorocarbons, and mixtures thereof.

16. The composition of claim 15 wherein said first part is a teat dip composition, a sterilant composition, an aseptic bottle wash composition or an animal skin treatment composition and the second part is an aqueous or a non-aqueous chlorite solution.

17. The composition of claim 13 wherein said first part is acidic and said second part is alkaline.

18. The composition of claim 13 wherein said composition after mixing said first and said second part has a pH of about 4–8.

19. The composition of claim 13 wherein said chlorite source is selected from the group consisting of salts of alkali metals, salts of alkaline earth metals, salts of transition metals, and mixtures thereof.

20. The composition of claim 13 wherein said first part, said second part or both are in a form selected from the group consisting of liquid, gas, aerosol, gel, lotion and solid.

21. The composition of claim 20 wherein said liquid is selected from the group consisting of bleach, biocide, laundry liquids and hard surface cleaners.

22. The composition of claim 20 wherein said lotion, liquid, solid or gel is a teat dip composition.

23. The composition of claim 20 wherein said solid is a soap composition for skin.

24. The composition of claim 13 wherein said solvent in the second part is selected from the group consisting of water, glycerin, sorbitol, $C_{1-22}$ carboxylic esters, $C_{1-10}$ carboxylic diesters, alcohols, glycols, ethers, liquid nonionic surfactants, aliphatic hydrocarbons, aromatic hydrocarbons, carbon dioxide, fluorocarbons, and mixtures thereof.

25. A biocidal or bleaching composition capable of generating chlorine dioxide comprising:
   a) at least one iodo-compound having at least one iodine atom said iodo-compound selected from the group consisting of an iodine containing interhalide, an iodine containing ionene resin, an organo-iodide, an organic iodophor, and mixtures thereof; and
   b) a source of chlorite ions at a concentration of more than about 6 wt-% to about 75 wt-%;
      wherein the molar ratio of chlorite ions to iodine atoms is 2 or greater.

26. A chlorine dioxide-generating composition useful as a biocide, or for bleaching, comprising:
   a) at least one iodo-compound having at least one iodine atom said iodo-compound selected from the group consisting of an iodine containing interhalide, an iodine containing ionene resin, an organo-iodide, an organic iodophor, and mixtures thereof; and
   b) a source of chlorite ions;
      wherein said molar ratio of chlorite ions to iodine atoms is 2 or greater for chlorine dioxide generation.

27. The composition of claim 26 wherein said composition is present at a concentration of 1 wt-% in aqueous solution and has a pH of about 1–9.

28. A method of reducing the microbial population on a surface comprising contacting said surface with an aqueous solution comprising about $5 \times 10^{-4}$ to about $7 \times 10^{2}$ grams/liter of the biocidal composition according to claim 26.

29. The method of claim 28 further comprising the step of agitation.

30. The method of claim 28 wherein said surface is selected from the group consisting of foods, plants, hard surfaces that come into contact with food, and animals.

31. The method of claim 30 wherein said animal is a bovine.

32. The method of claim 28 wherein said surface is a hard surface selected from a clean-in-place system, a clean-out-of-place system, a warewash machine, a sink, a package, an aseptic package, a food transportation vehicle, and food processing equipment.

33. The method of claim 28 wherein said method is effective against a microbe selected from the group consisting of Parvoviridae, Calciviridae, Herpesviridae, Paramyxoviridae, Mycobacterium spp, *Streptococcus pneumoniae*, *Psuedomonas aeruginosa*, *Listeria monocytongenes*, Aspergillus spp, *Staphylococcus aureus*, *Escherischia coli*, Salmonella spp, *Bacillus cerius* and a mastitis causing organism.

34. A method for the production of a biocidal or bleaching level of chlorine dioxide comprising the steps of:
   a) providing a source of chlorite ions;
   b) providing at least one iodo-compound having at least one iodine atom said iodo-compound selected from the group consisting of an iodine containing interhalide, an iodine containing ionene resin, an organo-iodide, an organic iodophor, and mixtures thereof;
      wherein the molar ratio of chlorite ions to iodine atoms is 2 or greater; and
   c) mixing a sufficient amount of the source of chlorite ions with a sufficient amount of said at least one iodo-compound to produce a biocidal or bleaching level of chlorine dioxide.

35. The method of claim 34 wherein said chlorine dioxide production occurs in a aqueous liquid environment.

36. The method of claim 35 wherein said pH of said aqueous liquid environnment is about 4–8.

37. The method of claim 34 wherein said chlorite ions and said iodo-compound are in a form selected from the group of solids, aqueous liquids, nonaqueous liquids, gels, gases and aerosols.

38. The method of claim 37 wherein said solid is a powder.

39. The method of claim 38 wherein the powder is a composition selected from the group consisting of a teat dip composition, a hard surface biocide composition, a hard surface bleach, a laundry bleach and a laundry biocide.

40. The method of claim 37 wherein said solid further comprises at least one solidifying agent selected from organic materials, inorganic materials and mixtures thereof.

41. The method of claim 40 wherein said solidifying agent is organic selected from polyethylene glycols, ureas, acetates, fatty acids, surfactants, defoamers, builders, and mixtures thereof.

42. The method of claim 40 wherein said solidifying agent is an inorganic hydratable salt selected from bicarbonates, carbonates, silicates, phosphates, sulfates and mixtures thereof.

43. The method of claim 40 wherein said solidifying agent is capable of binding free water.

\* \* \* \* \*